United States Patent

Sako et al.

[11] Patent Number: 6,037,169
[45] Date of Patent: *Mar. 14, 2000

[54] GARBAGE DISPOSAL APPARATUS

[75] Inventors: Toshiharu Sako; Takaharu Nakagawa; Manabu Mizobuchi, all of Osaka, Japan

[73] Assignee: Matsushita Electric Works, Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/822,705

[22] Filed: Mar. 21, 1997

[30] Foreign Application Priority Data

Mar. 25, 1996 [JP] Japan .................................. 8-067942

[51] Int. Cl.$^7$ .................................................. C12M 1/107
[52] U.S. Cl. .......................... 435/290.1; 435/286.6; 435/300.1; 422/4; 422/170; 422/171; 422/178
[58] Field of Search .............................. 435/266, 286.6, 435/289.1, 290.1, 291.1, 299.1, 300.1; 422/4, 5, 120, 122, 123, 125, 126, 170, 171, 177, 178; 423/224, 230, 231, 237, 238; 55/234, 256; 96/121–126, 130, 279, 351

[56] References Cited

U.S. PATENT DOCUMENTS

| | | | |
|---|---|---|---|
| 1,519,932 | 12/1924 | Reich ........................................ | 435/266 |
| 2,597,437 | 5/1952 | Bodamer . | |
| 3,216,905 | 11/1965 | Baptist ..................................... | 435/266 |
| 3,556,716 | 1/1971 | Pollio et al. . | |
| 4,179,412 | 12/1979 | Inaba et al. . | |
| 4,212,852 | 7/1980 | Aibe et al. . | |
| 4,273,749 | 6/1981 | Kimura et al. . | |
| 4,483,704 | 11/1984 | Easter, II .............................. | 435/290.4 |
| 5,145,581 | 9/1992 | Novy et al. . | |
| 5,160,707 | 11/1992 | Murray et al. . | |
| 5,254,512 | 10/1993 | Ueda et al. . | |
| 5,447,701 | 9/1995 | Inoue et al. . | |
| 5,472,676 | 12/1995 | Terui et al. . | |
| 5,496,730 | 3/1996 | Teramachi . | |
| 5,585,044 | 12/1996 | Kawakami et al. . | |
| 5,589,146 | 12/1996 | Morii et al. . | |
| 5,743,940 | 4/1998 | Sugo et al. . | |

FOREIGN PATENT DOCUMENTS

| | | |
|---|---|---|
| 0 476 135 | 3/1992 | European Pat. Off. . |
| 0 514 729 | 11/1992 | European Pat. Off. . |
| 94 27932 | 12/1994 | WIPO . |
| 96 07624 | 3/1996 | WIPO . |

OTHER PUBLICATIONS

Patent Abstracts of Japan, vol. 003, No. 072 (C–049), Jun. 21, 1979 & JP 54 046187 A (Hitachi Zosen Corp.), Apr. 11, 1979 *abstract.

*Primary Examiner*—William H. Beisner
*Attorney, Agent, or Firm*—Sughrue, Mion, Zinn, Macpeak & Seas, PLLC

[57] ABSTRACT

A garbage disposal apparatus having a processing chamber for processing garbage; and a purifying chamber for purifying gas discharged from the processing chamber and containing stinking components, wherein the process of garbage in the processing chamber is performed by decomposition using microorganisms, the purifying chamber has a plurality of zones, a first purifying chamber connected to the processing chamber is provided with an ammonia purifying unit for purifying ammonia and a second purifying chamber into which gas allowed to pass through the first purifying chamber is introduced is provided with a non-ammonia purifying unit for purifying non-ammonia gas. Ammonia contained in a high concentration and having a large threshold is first removed in the first purifying chamber. Then, non-ammonia contained at a low concentration and having a small threshold is removed. Therefore, an excellent purifying efficiency can be realized.

29 Claims, 9 Drawing Sheets

GARBAGE DISPOSAL APPARATUS

BACKGROUND OF THE INVENTION

1. Field of the Invention

The present invention relates to a garbage disposal apparatus, and more particularly to a garbage disposal apparatus having a garbage processing chamber adapted to decomposition, using microorganisms.

2. Related Art

Garbage can be disposed of by both a dry method and a decomposition method using microorganisms. The dry method involves removing water in the garbage, and gas being generated from the garbage when the water is evaporated. The gas contains components selected from nitrogen compounds, such as ammonia and amine, sulfur compounds, such as methyl sulfide, methyl mercaptan and methyl disulfide, and aldehydes. On the other hand, the decomposition method using microorganisms is able to decompose the garbage into water, carbon dioxide and ammonia if the decomposition is completely performed. However, the adjustment of temperature, the amount of retained water and that of oxygen to control an optimum state for microorganisms to decompose the garbage, cannot easily be performed. Therefore, a malodorous gas similar to that generated with the dry method, is generated.

The malodorous components have varying thresholds for respective components. The threshold means a concentration limit at which a distinction from odorless air cannot be perceived. Gas having a threshold of 0.001 ppm cannot be distinguished from odorless air if the concentration is 0.001 ppm or lower. That is, the gas does not smell. If a malodorous component of 1 ppm having a threshold of 0.001 ppm is contained in the gas, the component is required to have a concentration of $\frac{1}{1000}$ or lower. The simplest method to make the gas an odorless gas is to dilute the malodorous component 1000 times.

If garbage of the foregoing type is processed by the decomposition method using microorganisms, the gas generated mixedly contains components, such as ammonia, which are contained in a large quantity and which have relatively large thresholds, and components, such as sulfur components, which are contained in a small quantity and which have significantly small thresholds. For example, ammonia contained in the generated gas at about 100 ppm has a threshold of about 10 ppm. If removal by dilution to $\frac{1}{10}$ is performed, the odor of ammonia can be prevented. On the other hand, the overall portion of the generated gas is a large value of about 5000 (the diluting magnification at which a distinction from odorless air cannot be perceived). Therefore, dilution to 5000 times is required to make the malodorous component above be perceived as odorless.

Therefore, if garbage is processed by the decomposition method using microorganisms and gas generated during the process is made to be odorless, dilution to 5000 times is required or the malodorous component must be reduced to $\frac{1}{5000}$. The dilution of 5000 times requires a large scale air fan. If activated charcoal is used in the removal process, ammonia generated in a large quantity is adsorbed by the activated charcoal. Thus, the adsorption life-time is too short. If a catalyst is used in the purifying the process, a large quantity of catalyst is required to purify ammonia. Moreover, the gas must be heated to high temperatures in order to cause the catalyst to exhibit its functions. In addition, a large running cost is required. Also a purifying process using ozone requires a large size ozone generator and a large quantity of ozone decomposing catalyst.

SUMMARY OF THE INVENTION

In view of the foregoing, an object of the present invention is to provide a garbage disposal apparatus for processing garbage by decomposition using microorganisms which is capable of satisfactorily purifying malodorous components for a long time.

In an aspect of the present invention, there is provided a garbage disposal apparatus comprising a processing chamber for processing garbage; and a purifying chamber for purifying gas discharged from the processing chamber and containing malodorous components, wherein the process of garbage in the processing chamber is performed by decomposition using microorganisms, the purifying chamber has a plurality of zones, and a first purifying chamber which is connected to the processing chamber is provided with an ammonia purifying unit for purifying ammonia, and a second purifying chamber into which gas, allowed to pass through the first purifying chamber, is introduced, is provided with a non-ammonia purifying unit for purifying non-ammonia gas. As a result of the structure above, ammonia contained in a high concentration and having a large threshold is first removed. Then, non-ammonia contained at a low concentration and having a small threshold is removed. Therefore, an excellent purifying efficiency can be realized.

In another aspect of the present invention, there is provided a garbage disposal apparatus having a structure such that the first purifying chamber 11 has a unit 11 having a mechanism for bringing ammonia into contact with water or a water solution. As a result of the above-mentioned structure, ammonia can easily be removed.

In another aspect of the present invention, there is provided a garbage disposal apparatus having a structure such that the first purifying chamber has a water storage tank for storing water or water solution and gas discharged from the processing chamber is introduced into the water storage tank.

In another aspect of the present invention, there is provided a garbage disposal apparatus having a structure such that the water solution which is brought into contact with the ammonia is a water solution containing cation exchange resin. As a result, performance for solving ammonia can be improved and therefore satisfactory purifying performance can be obtained.

In another aspect of the present invention, there is provided a garbage disposal apparatus having a structure such that the water solution which is brought into contact with the ammonia is acid water solution. As a result, performance for solving ammonia can be improved and therefore a satisfactory purifying performance can be obtained.

In another aspect of the present invention, there is provided a garbage disposal apparatus having a structure such that a dehumidifying unit is provided in a gas-flow passage connecting the first purifying chamber and the second purifying chamber to each other. Deterioration of the function of the non-ammonia purifying unit caused from humidity can be prevented.

In another aspect of the present invention, there is provided a garbage disposal apparatus having a structure such that the first purifying chamber has an adsorbent layer, and a passage for gas allowed to pass through the adsorbent layer has a catalyst layer for ammonia. As a result, ammonia can easily be purified without the necessity of supplying water and discharging water. Ammonia can be desorbed from the adsorbent layer so as to be regenerated.

In another aspect of the present invention, there is provided a garbage disposal apparatus having a structure such that an introduction passage for introducing gas discharged from the processing chamber into the adsorbent layer is provided with an inlet opening, and opening/closing means for arbitrarily introducing/stopping outer air from the inlet opening and gas introduced from the introduction passage, is provided.

In another aspect of the present invention, there is provided a garbage disposal apparatus having a structure such that the gas-flow passage having the catalyst layer for ammonia and a gas-flow passage connected to the second purifying chamber are branched, and opening/closing means is provided which is capable of arbitrarily introducing/stopping gas allowed to pass through the adsorbent layer to the gas-flow passages. As a result, the non-ammonia purifying unit can be protected and deterioration in the function can be prevented.

In another aspect of the present invention, there is provided a garbage disposal apparatus having a plurality of purifying units each consisting of the first purifying chamber and the second purifying chamber, and the purifying units are disposed in parallel. As a result, the regeneration of the adsorbent layer and the purification of gas can alternately be performed by the foregoing purifying units. Purification of the gas can always be performed.

In another aspect of the present invention, there is provided a garbage disposal apparatus having a structure such that the purifying chamber is divided into a purifying passage and a regeneration passage by a partition plate, the adsorbent layer formed to traverse the purifying passage and the regeneration passage is rotated around a central shaft provided for the partition plate, the purifying passage is provided with the second purifying chamber having the adsorbent layer and a non-ammonia purifying unit, and the regeneration passage has the inlet opening, the adsorbent layer and the catalyst layer for ammonia. As a result of the foregoing structure in which the adsorbent layer is rotated, the adsorbent layer is able to adsorb ammonia in the purifying passage and is regenerated in the regeneration passage.

In another aspect of the present invention, there is provided a garbage disposal apparatus having a structure such that a heating unit for heating the first purifying chamber is provided. As a result, the desorption and process of ammonia can be enhanced, and the adsorbent layer can easily be regenerated.

In another aspect of the present invention, there is provided a garbage disposal apparatus having a structure such that an adsorbent forming the adsorbent layer is selected from the group consisting of activated alumina, natural zeolite, synthetic zeolite, silica gel, activated clay, accretion activated charcoal and ion exchange resin. As a result, performance for adsorbing ammonia can be improved.

In another aspect of the present invention, there is provided a garbage disposal apparatus having a structure such that the catalyst layer for ammonia is in the form in which a carrier includes a noble metal or a metal oxide.

In another aspect of the present invention, there is provided a garbage disposal apparatus having a structure such that the adsorbent layer includes a noble metal or metal oxide for forming the catalyst layer for ammonia, and the adsorbent layer also serves as the catalyst layer for ammonia. As a result, the apparatus can be simplified.

In another aspect of the present invention, there is provided a garbage disposal apparatus having a structure such that the noble metal is selected from the group consisting of platinum, gold, silver, copper, palladium, ruthenium and rhodium.

In another aspect of the present invention, there is provided a garbage disposal apparatus having a structure such that the metal oxide is selected from the group consisting of nickel oxide, manganese oxide, cobalt oxide, iron oxide and vanadium pentoxide.

In another aspect of the present invention, there is provided a garbage disposal apparatus having a structure such that the non-ammonia purifying unit has an adsorbent layer for non-ammonia.

In another aspect of the present invention, there is provided a garbage disposal apparatus having a structure such that an adsorbent for forming the adsorbent layer for non-ammonia is activated charcoal. As a result, the efficiency for removing non-ammonia gas can be improved and handling can be facilitated.

In another aspect of the present invention, there is provided a garbage disposal apparatus having a structure such that the non-ammonia purifying unit has a catalyst layer for non-ammonia made of a catalyst having oxidizing performance. As a result, the performance for purifying non-ammonia can semi-permanently be maintained.

In another aspect of the present invention, there is provided a garbage disposal apparatus having a structure such that the catalyst is in the form in which a carrier includes at least any one of the noble metals selected from the group consisting of platinum, gold, silver, copper, palladium, ruthenium and rhodium, and a metal oxide selected from the group consisting of nickel oxide, manganese oxide, cobalt oxide, iron oxide and vanadium pentoxide.

BRIEF DESCRIPTION OF THE DRAWINGS

FIG. 10 (a) is a schematic view showing an essential portion of the garbage disposal apparatus according to the embodiment of the present invention;

FIG. 10 (b) is a schamatic view showing an essential portion of the garbage disposal apparatus, as shown in FIG. 10 (a), with heat device;

DETAILED DESCRIPTION OF THE PREFERRED EMBODIMENTS

Figure 1:
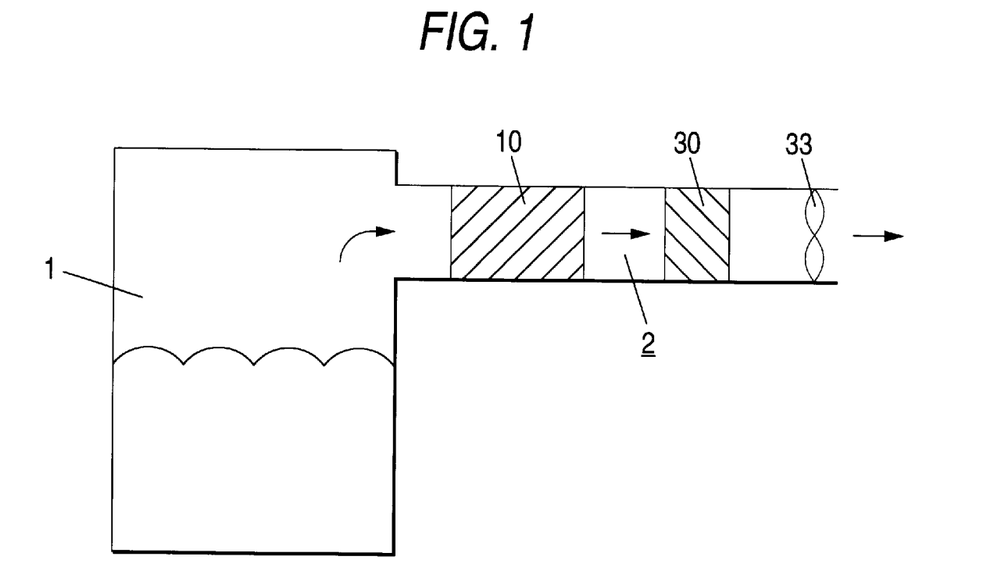
FIG. 1 is a block diagram schematically showing the garbage disposal apparatus according to the present invention.

The present invention will now be described. FIG. 1 is a block diagram schematically showing a garbage disposal apparatus according to the present invention.

The garbage disposal apparatus according to the present invention has a processing chamber 1 for processing garbage by decomposition using microorganisms. Gas generated during the foregoing process contains ammonia in a large quantity and non-ammonia gas, such as sulfur compounds in a small quantity as malodorous components. Specifically, ammonia is 99 volume % of the malodorous components in the generated gas. According to the present invention, there is provided an apparatus capable of purifying the foregoing malodorous gas and maintaining the required performance for a long time.

The structure according to the present invention has a purifying chamber 2 for purifying gas containing the malodorous components discharged from the processing chamber 1. The purifying chamber 2 has a first purifying chamber 10 and a second purifying chamber 30. The first purifying chamber 10 connected to the processing chamber 1 has an ammonia purifying unit for purifying ammonia. The second purifying chamber 30 into which gas allowed to pass through the first purifying chamber 10 is introduced, has a non-ammonia purifying unit for purifying non-ammonia gas. The garbage disposal apparatus having the foregoing structure is arranged such that gas containing malodorous components is first introduced into the first purifying chamber 10 by an air fan 33 so that ammonia contained at a high concentration and having a large threshold is removed by the ammonia purifying unit. Then, the gas is introduced into the second purifying chamber 30 in which non-ammonia gas contained at a low concentration and having a small threshold is removed by the non-ammonia purifying unit. Since ammonia contained in a large quantity is first removed, deterioration of the non-ammonia purifying unit by ammonia and the like can be prevented. Therefore, the function of the non-ammonia purifying unit can satisfactorily be maintained for a long time. Moreover, the ammonia purifying unit and the non-ammonia purifying unit can be operated efficiently. Note that arrows indicate the direction in which the malodorous gas moves.

Figure 2:
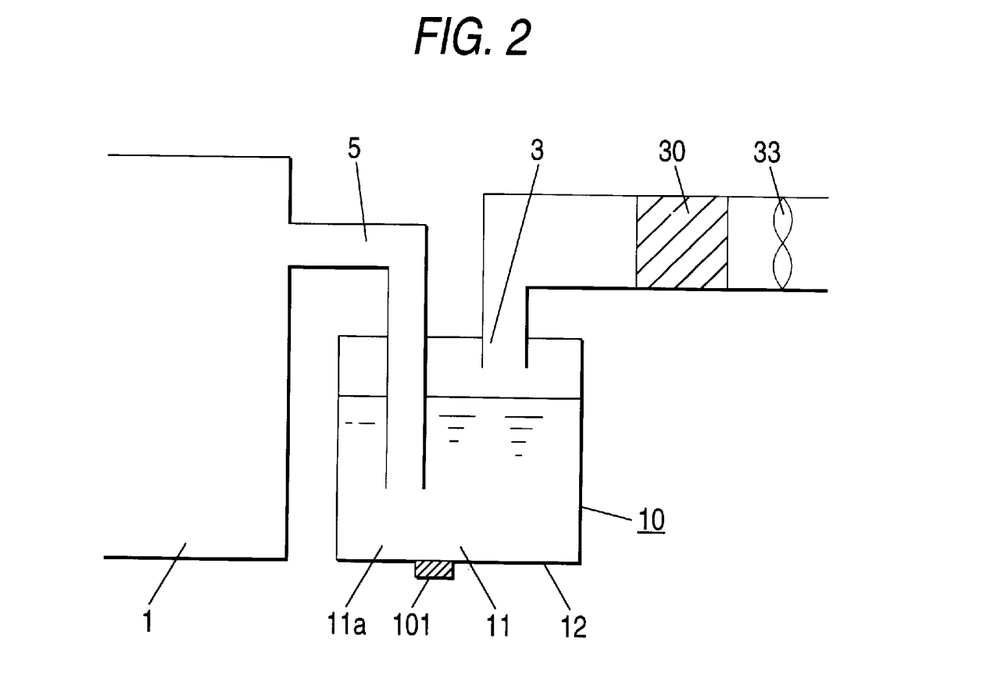
FIG. 2 is a schematic view showing an essential portion of the garbage disposal apparatus according to the embodiment of the present invention.

The first purifying chamber 10 for purifying ammonia will now be described. FIG. 2 is a schematic view showing an essential portion of the garbage disposal apparatus according to a first embodiment of the present invention. The first purifying chamber 10 of the apparatus according to this embodiment has a water storage tank 12 storing water solution 11a as a unit 11 having a function for contact with water or water solution (hereinafter called "water solution").

The leading end of an introduction passage 5 for the gas discharged from the processing chamber 1 reaches the inside portion of the water solution 11a stored in the water storage tank 12. Moreover, a gas-flow passage 3 connected to the second purifying chamber 30 is disposed above the water level in the water storage tank 12. Gas discharged from the processing chamber 1 is allowed to pass through the introduction passage 5 so as to be introduced into the water solution 11a so that ammonia is dissolved in the water solution 11a so as to be removed. If a water supply port and a discharge port (not shown) are provided for the water storage tank 12, the water solution 11a can easily be changed. Thus, the apparatus can easily be handled. If the water solution 11a stored in the water storage tank 12 is water solution containing cation exchange resin, the performance for dissolving ammonia can be improved. Therefore, even if the concentration of ammonia to be discharged is high, excellent removing performance can be maintained.

If the water solution 11a stored in the water storage tank 12 is acid water solution, ammonia can be neutralized. Therefore, the removing performance can be improved and the water solution can be used for a long time. If the water solution 11a is water, there is a risk that the dissolved ammonia is again discharged. If it is once neutralized, it is converted into ammonia salt, thus overcoming the risk of the re-discharge. It is preferable that the acid water solution be weak acid because the safety and the corrosion resistance of the container must be considered. The water solution is selected from the group consisting of buffer solution having a buffering function, such as tartrate, phthalate, phosphate, acetate, citrate, ascorbic acid, citric acid, malic acid and succinic acid.

If vibrations of ultrasonic waves or the like are applied to the water solution 11a in the water storage tank 12 by using a ultrasonic device 101 or the like, the removing performance can furthermore be improved.

Figure 3:
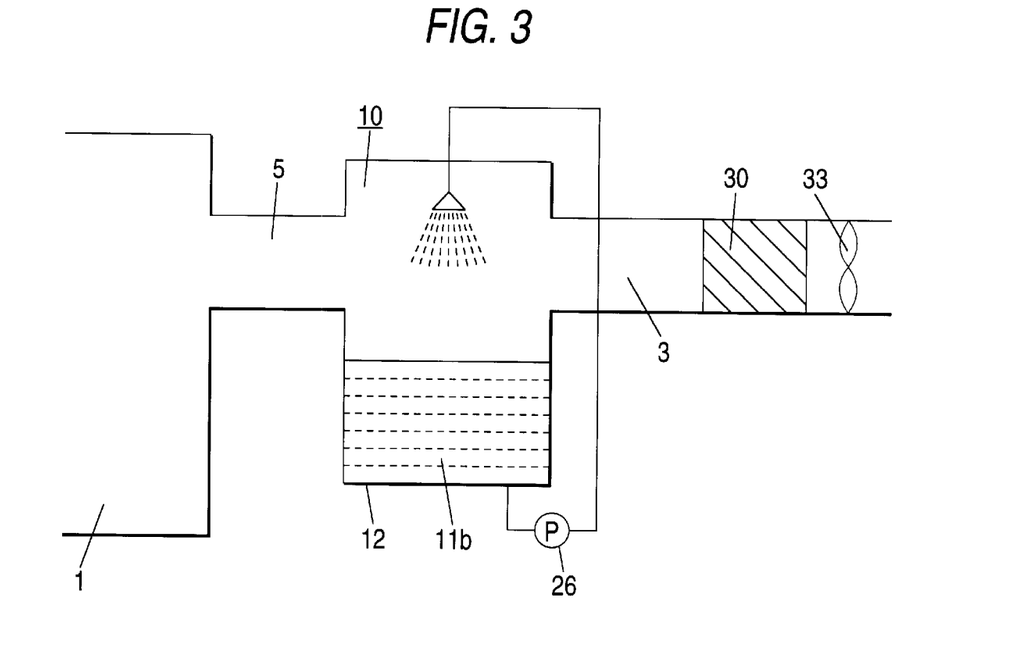
FIG. 3 is a schematic view showing an essential portion of the garbage disposal apparatus according to the embodiment of the present invention.
Figure 4:
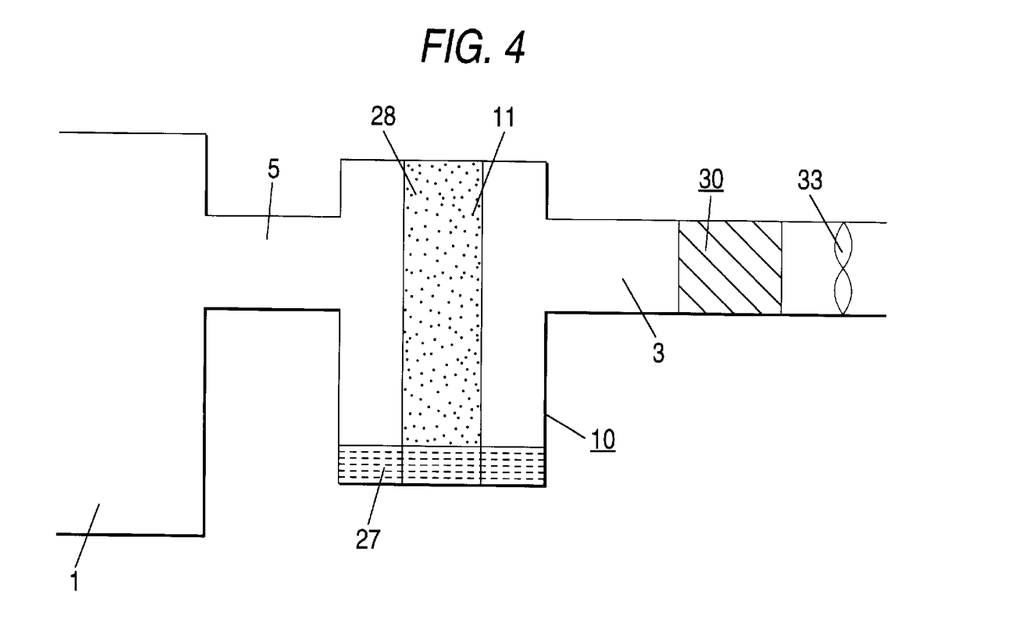
FIG. 4 is a schematic view showing an essential portion of the garbage disposal apparatus according to the embodiment of the present invention.

The apparatus for dissolving ammonia to remove the same is not limited to the structure in which gas is introduced into water. FIGS. 3 and 4 are schematic views showing garbage disposal apparatuses according to second and third embodiments of the present invention. As shown in FIG. 3, the first purifying chamber 10 has a water storage tank 12 storing water solution 11b. Water 11b in the water storage tank 12 is sucked by a pump 26 so as to be sprayed from the top surface of the first purifying chamber 10. Gas discharged from the processing chamber 1 is allowed to pass through the first purifying chamber 10 in which water solution is being sprayed so that ammonia is removed.

As shown in FIG. 4, a fiber or sponge layer 28 transversing the first purifying chamber 10 is provided. A water tank storing water solution 27 is provided at the base portion of the layer above. The water solution 27 in the water tank is absorbed into the layer 28 by the capillary phenomenon. Gas discharged from the processing chamber 1 is allowed to pass through the layer 28 so that ammonia is removed.

Figure 5:
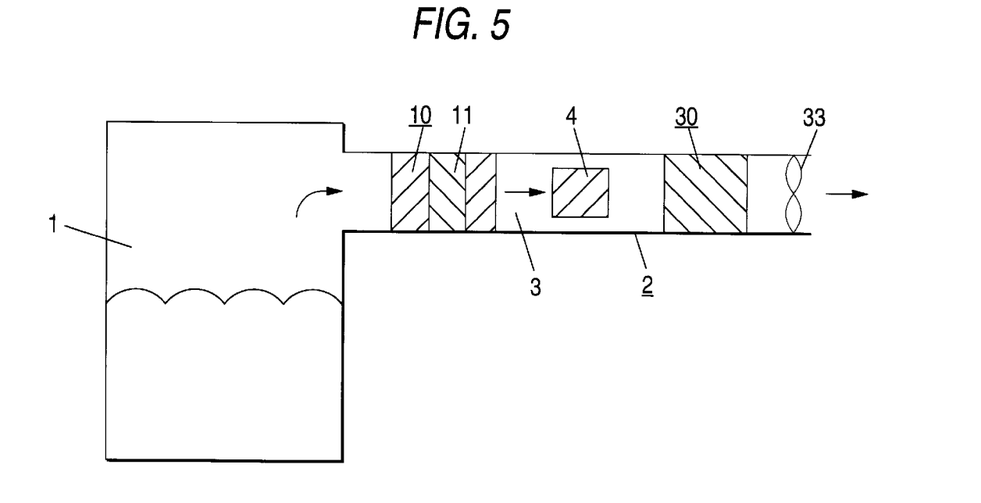
FIG. 5 is a block diagram schematically showing the garbage disposal apparatus according to another embodiment of the present invention.

The gas, from which ammonia has been removed, contains water therein in a large quantity. The gas allowed to pass through the first purifying chamber 10 is introduced into the second purifying chamber 30. If the quantity of water is too large, the functions of some non-ammonia purifying units deteriorate. An embodiment having a contrivance to solve the foregoing problem will now be described. FIG. 5 is a block diagram schematically showing another embodiment of the garbage disposal apparatus according to the present invention. As shown in FIG. 5, the garbage disposal apparatus has a dehumidifying unit 4 disposed in a gas-flow passage 3 connecting the first purifying chamber 10 and the second purifying chamber 30 to each other. As the dehumidifying unit 4, there is considered an apparatus which cools the gas to remove the same by moisture condensation, a heating apparatus for lowering the relative humidity of the gas, and an apparatus having an adsorbing layer made of silica gel, zeolite, synthetic zeolite, silica gel, activated alumina or calcium chloride.

Figure 6:
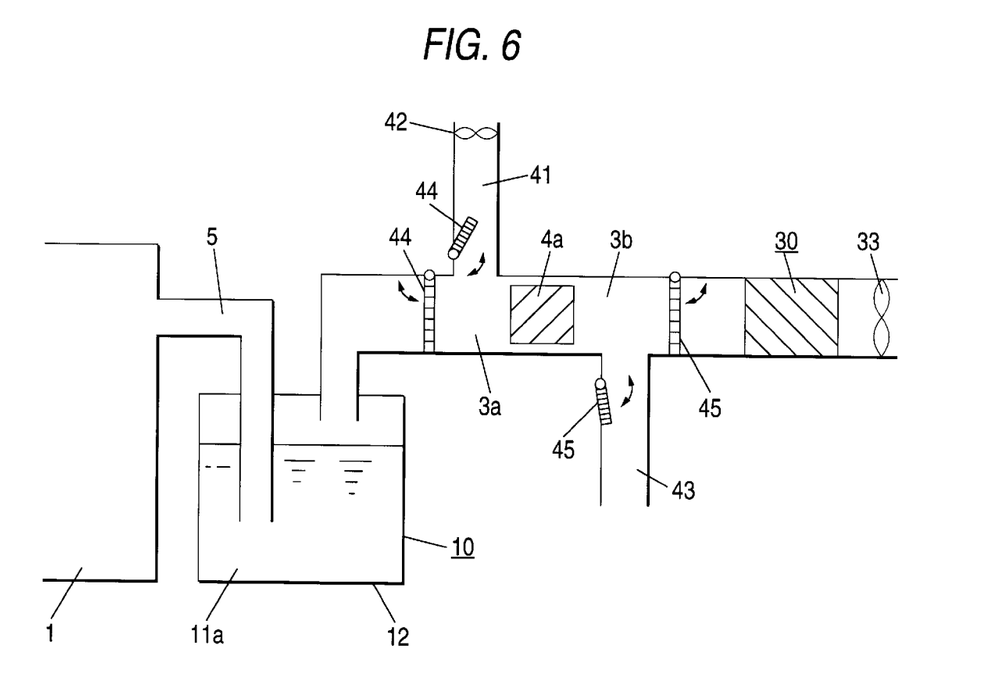
FIG. 6 is a schematic view showing an essential portion of the garbage disposal apparatus according to the embodiment of the present invention.

If the dehumidifying unit 4 is an apparatus having the adsorbing layer, it is preferable that a structure for regenerating the adsorbing layer be employed. FIG. 6 is a schematic view showing an essential portion of a garbage disposal apparatus having the dehumidifying unit 4 which is an adsorbent layer 4a. An air-inlet passage 41 and an air fan 42 for newly introducing air from outside are provided for a gas-flow passage 3a between the ammonia purifying unit and the adsorbent layer 4a. Moreover, a discharge passage 43 is provided for an air-flow passage 3b between the adsorbent layer 4a and the non-ammonia purifying unit. An opening/closing means 44 for arbitrarily introducing/stopping air from the air-inlet passage 41 and gas from the gas-flow passage 3a is provided at the branched position of the air-inlet passage 41. An opening/closing means 45 for arbitrarily supplying/stopping air to the discharge passage 43 and supplying/stopping gas to the air-flow passage 3b is provided at the branched position of the discharge passage 43. In a normal state, the air-inlet passage 41 and the discharge passage 43 are closed so that gas allowed to pass through the first purifying chamber 10 is allowed to pass through the adsorbent layer 4a so as to be introduced into the second purifying chamber 30. If the adsorbent layer 4a is required to be regenerated, the air-inlet passage 41 and the discharge passage 43 are closed to introduce fresh air into the adsorbent layer 4a and air allowed to pass through the adsorbent layer 4a is discharged from the discharge passage 43 to the outside.

Figure 7:
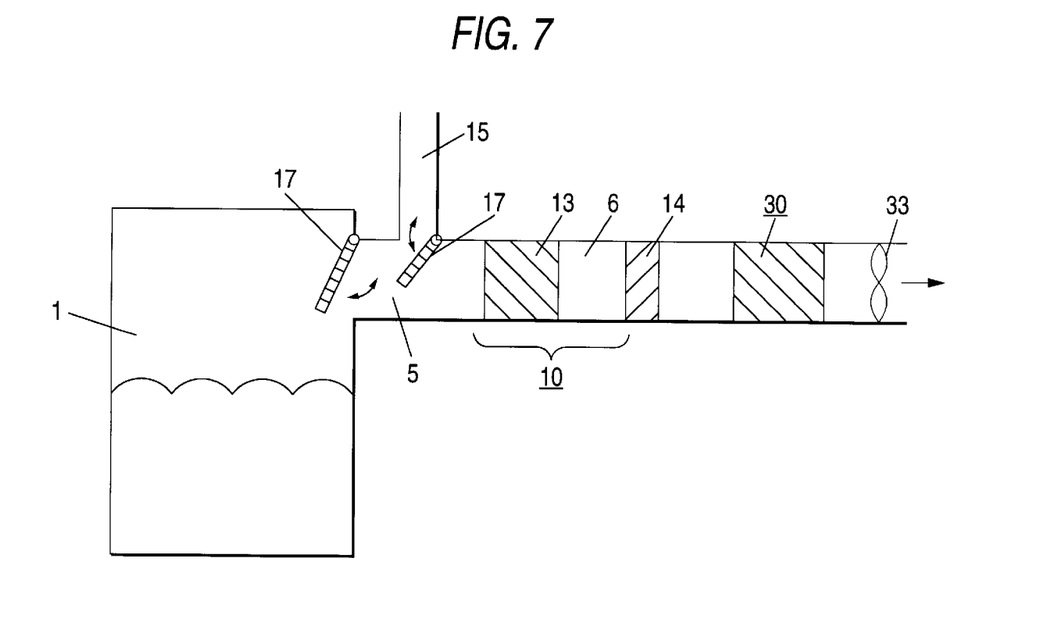
FIG. 7 is a block diagram schematically showing the garbage disposal apparatus according to another embodiment of the present invention.

A structure in which the first purifying chamber 10 for purifying ammonia is provided with an ammonia purifying unit except the unit 11 will now be described, the ammonia purifying unit having a function for realizing contact with water or water solution. FIG. 7 is a block diagram showing the schematic structure of another garbage disposal apparatus according to the present invention. As shown in FIG. 7, the garbage disposal apparatus has an adsorbent layer 13 in the first purifying chamber 10; and a catalyst layer 14 for ammonia in the gas-flow passage 6 for the gas allowed to pass through the adsorbent layer 13. Moreover, the foregoing processing apparatus has an inlet opening 15 in an introduction passage 5 for introducing gas discharged from the processing chamber 1 into the adsorbent layer 13. Moreover, an opening/closing means 17 for arbitrarily introducing/stopping outer air from the inlet opening 15 and the gas introduced from the introduction passage 5 is formed. The adsorbent layer 13 has excellent performance for quickly adsorbing ammonia. Although the catalyst layer 14 for ammonia cannot absorb ammonia as quickly as the adsorbent layer 13, it is a catalyst having a function for purifying ammonia. If a large quantity of ammonia is adsorbed to the adsorbent layer 13 and thus the function deteriorates, the catalyst layer 14 for ammonia has a function of processing ammonia and processing desorbed ammonia when ammonia has been desorbed from the adsorbent layer 13 in order to regenerate the adsorbent layer 13.

As the adsorbent for forming the adsorbent layer 13, activated alumina, natural zeolite, silica gel, activated clay, accretion activated charcoal and ion exchange resin are used. The adsorbent layer 13 is formed by at least one of the materials above. Among the materials above, silica gel is a most suitable material. If 1g of silica gel and 1g of synthesized zeolite are used to compare the break-through period (time taken for adsorption to be saturated and removal ratio to be made to be zero), a malodorous gas containing ammonia in a quantity of 100 ppm and supplied with air at a flow rate of 200 cc/minute results in the synthesized zeolite to be broken-through in two hours. On the other hand, silica gel is able to maintain the adsorbing performance for 25 hours.

As the catalyst layer 14 for ammonia, a structure is selected from a structure in which the carrier includes a noble metal or a metal oxide having oxidizing performance. The carrier is selected from the group consisting of alumina, titania, silica alumina, silica and zeolite. The noble metal is selected from the group consisting of platinum, gold, silver, copper, palladium, ruthenium and rhodium. Among the foregoing materials, platinum is the most suitable material. The metal oxide is selected from the group consisting of nickel oxide, manganese oxide, cobalt oxide, iron oxide and vanadium pentoxide. Although the catalyst layer 14 for ammonia cannot quickly adsorb ammonia as can be performed by the adsorbent layer 13 at room temperature, it is able to remove a large quantity of ammonia if it is heated to, for example, 200° C. to 300° C.

The garbage disposal apparatus has a structure in which the inlet opening 15 is closed in a normal state, and the malodorous gas generated in the processing chamber 1 is introduced from the introduction passage 5 to cause the same to pass through the adsorbent layer 13. After ammonia has been adsorbed, the gas is introduced into the second purifying chamber 30. When the adsorbent layer 13 has been saturated with ammonia and it must be regenerated, introduction of the malodorous gas from the introduction passage 5 is interrupted and the inlet opening 15 is opened so as to introduce fresh air in order to desorb ammonia adsorbed to the adsorbent layer 13 so as to regenerate the adsorbent layer 13. After the adsorbent layer 13 has been regenerated, the inlet opening 15 is closed to introduce, from the introduction passage 5, malodorous gas generated in the processing chamber 1. Since the adsorbent layer 13 and the catalyst layer 14 for ammonia are provided as described above, the adsorbent layer 13 can be regenerated in a state where the adsorbent layer 13 is quickly adsorbing ammonia. Therefore, the purifying operation can satisfactorily be performed for a long time.

Figure 8:
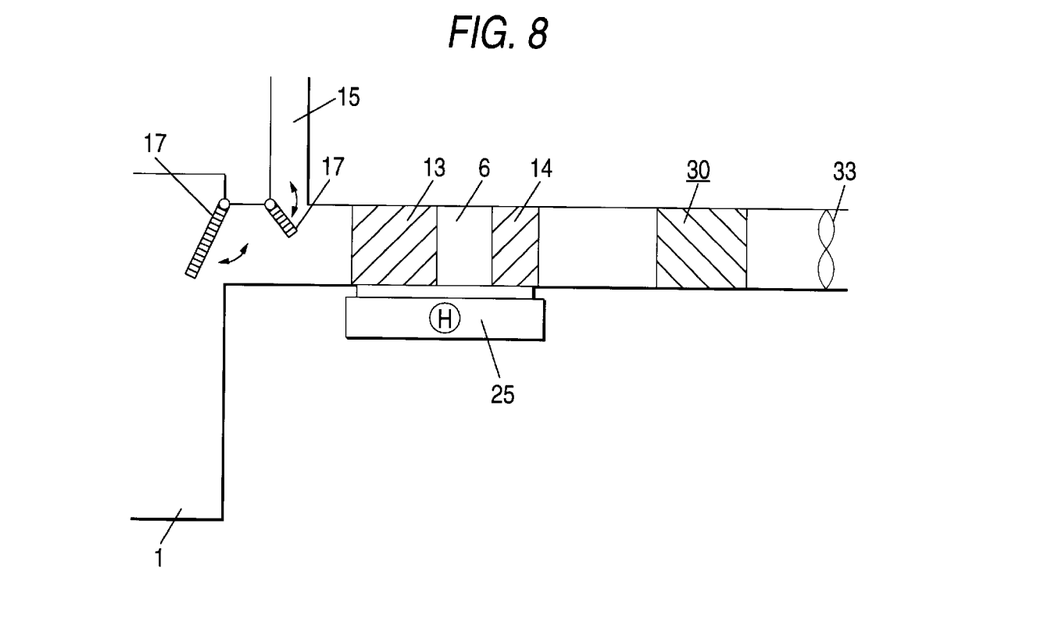
FIG. 8 is a schematic view showing an essential portion of the garbage disposal apparatus according to the embodiment of the present invention.
Figure 9:
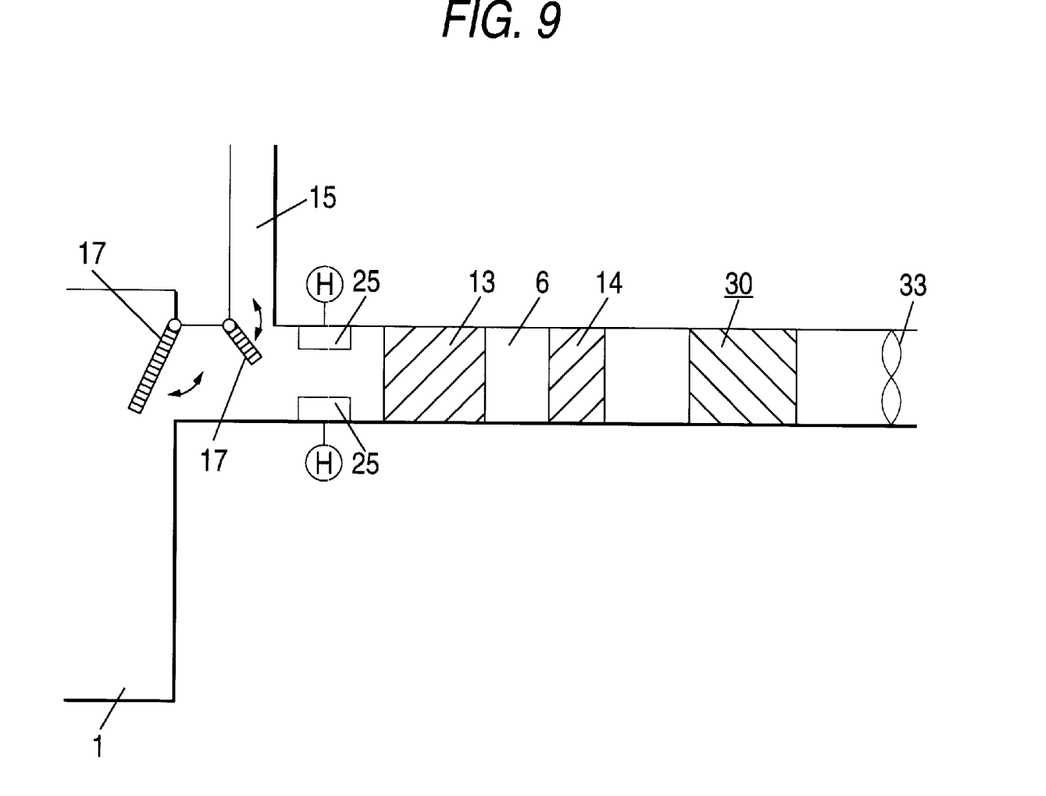
FIG. 9 is a schematic view showing an essential portion of the garbage disposal apparatus according to the embodiment of the present invention.

Since the adsorbent layer 13 and the catalyst layer 14 for ammonia are heated, the desorption and the process of ammonia can be enhanced, and it is preferable that the foregoing apparatus be provided with a heating unit for heating the first purifying chamber 10. FIGS. 8 and 9 are schematic views showing an essential portion of a purifying unit according to another embodiment of the present invention. As shown in FIG. 8, in the foregoing processing apparatus a heating unit 25 is disposed in connection with the adsorbent layer 13 and the catalyst layer 14 for ammonia. When regeneration is performed, the heating unit 25 is operated to raise the temperature of the adsorbent layer 13 and the catalyst layer 14 for ammonia. As shown in FIG. 9, the heating unit 25 may be disposed between the inlet opening 15 and the adsorbent layer 13 to heat air introduced through the inlet opening 15 so as to heat the adsorbent layer 13. If the heating unit 25 is provided, the desorption and process of ammonia can be enhanced. Therefore, the regeneration of the adsorbent layer 13 can easily be performed so that the removing performance is maintained for a long time. Note that the heating unit 25 is omitted in the following drawings for explaining the apparatus.

Figure 10:
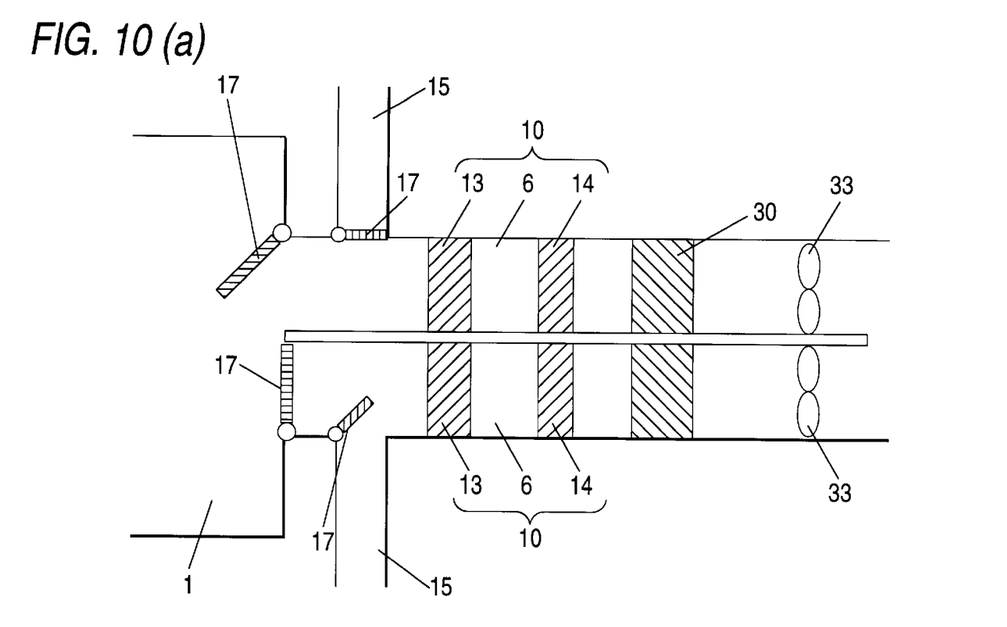

In the foregoing garbage disposal apparatus, purification of gas generated in the processing chamber 1 and regeneration of the adsorbent layer 13 are repeated. Therefore, a garbage disposal apparatus having a plurality of purifying units each consisting of the first purifying chamber 10 and the second purifying chamber 30 is shown in FIG. 10 (*a*). Since the foregoing purifying units are disposed in parallel in the processing apparatus above, the regeneration of the adsorbent layer 13 and purification of the gas can alternately be performed in the purifying unit by operating the opening/closing means 17. Therefore, the purification of the malodorous gas can always be performed.

FIG. 10(*b*) shows an example performed by using two purifying units described above. The adsorbent layer employs silica gel within 300 g, the catalyst layer 14 is provided with the carrier having platinum in 40 cc, and the second purifying chamber 30 employs a catalyst with the carrier having platinum in 30 cc. In this condition, purification of the gas discharged from the processing chamber and regeneration of the adsorbent layer are alternatively processed in each unit per 12 hours cycle. When the purification is preformed, the duct communicated with the processing chamber is opened by using the opening/closing means 17 and the inlet opening 15 is closed. Further, heating device 251 is in off and heating device 252 is at 150° C. When the regeneration is performed, the duct communicated with the processing chamber is closed by using the opening/closing means 17 and the inlet opening 15 is opened. Further, the heating device 251 is at 250° C. and the heating device 252 is at 150° C. The device is located into the room temperature condition.

Figure 15:
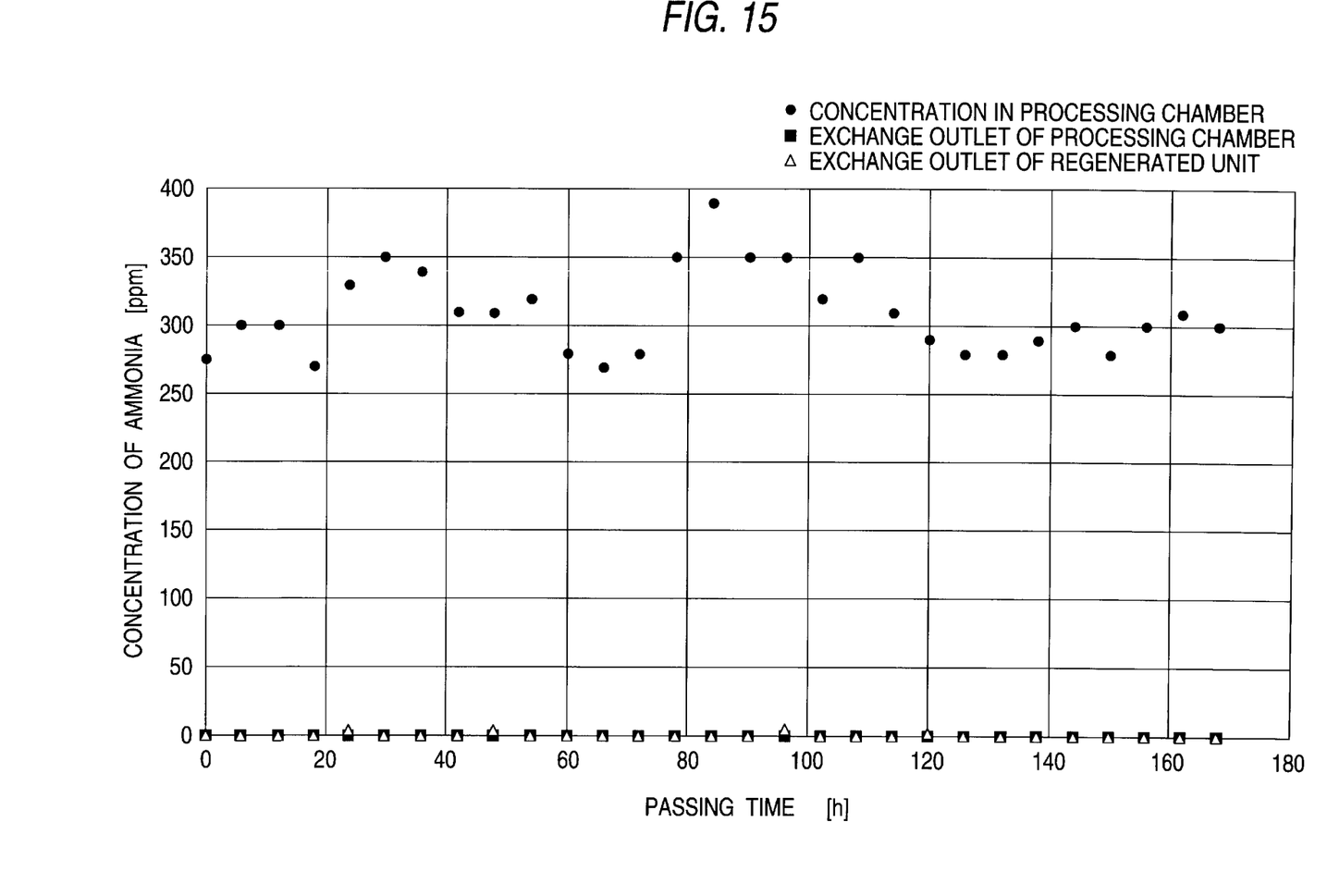
FIG. 15 is a graph showing a result of a purification characteristic value.

FIG. 15 shows a result of purification characteristic value under the condition of alternatively processing the purification and the regeneration per 12 hours cycle. The removing performance subjected to the ammonia discharged from the processing chamber is used as a purification characteristic.

In view of FIG. 15, the purification characteristic is not deteriorated under the condition of alternatively processing the purification and the regeneration per 12 hours cycle.

Figure 11:
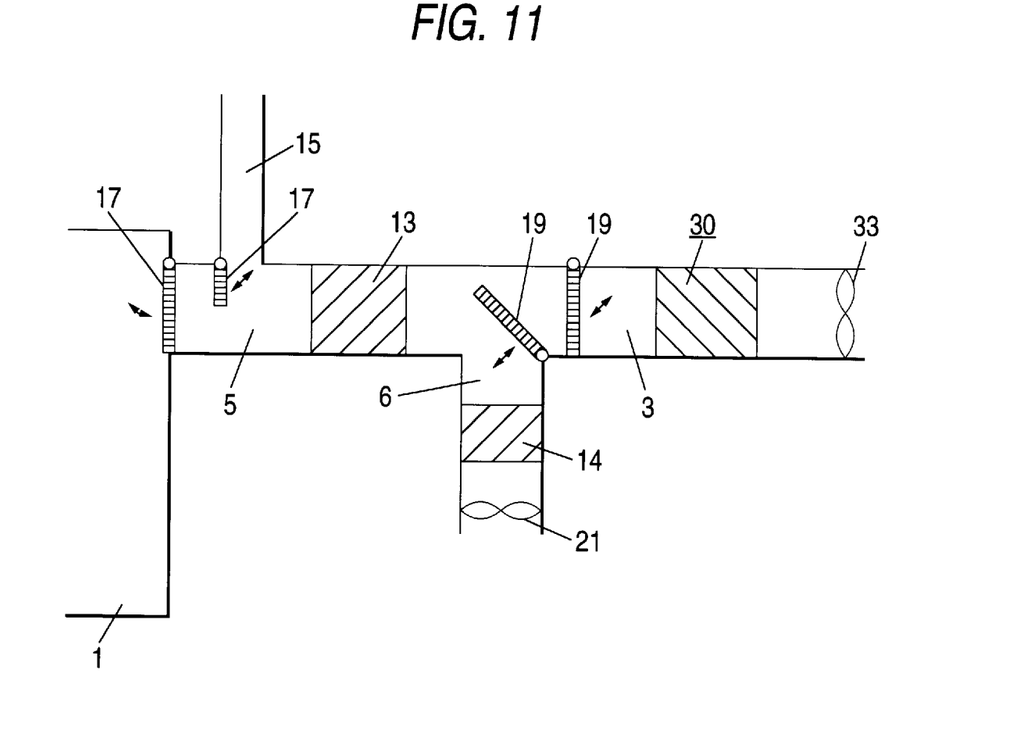
FIG. 11 is a schematic view showing an essential portion of the garbage disposal apparatus according to the embodiment of the present invention.

Another embodiment of the garbage disposal apparatus having the adsorbent layer 13 will now be described. FIG. 11 is a schematic view showing an essential portion of a garbage disposal apparatus according to another embodiment of the present invention. Different structures from the foregoing structures will now be described. As shown in FIG. 11, the gas-flow passage 6 having the catalyst layer 14 for ammonia and the gas-flow passage 3 connected to the second purifying chamber 30 are branched. An opening/closing means 19 is formed at the position at which the gas-flow passages 3 and 6 are branched so that the introduction of gas allowed to pass through the adsorbent layer 13 and stoppage of the same are arbitrarily performed. The air-flow passages 3 and 6 respectively have air fans 33 and 21. In the garbage disposal apparatus, the inlet opening 15 and the gas-flow passage 6 having the catalyst layer 14 for ammonia are usually closed. Thus, the gas processed in the processing chamber 1 is introduced from the introduction passage 5, and then allowed to pass through the adsorbent layer 13. The gas, from which ammonia has been adsorbed, is allowed to pass through the gas-flow passage 3 so as to be introduced into the second purifying chamber 30. If regeneration of the adsorbent layer 13 is required, gas from the introduction passage 5 is stopped. Also the gas-flow passage 3 connected to the second purifying chamber 30 is closed. By opening the inlet opening 15, fresh air is introduced to desorb ammonia adsorbed to the adsorbent layer 13 so as to regenerate the adsorbent layer 13. Moreover, the gas-flow passage 6 having the catalyst layer 14 for ammonia is opened to cause the catalyst layer 14 for ammonia to remove desorbed ammonia. After the adsorbent layer 13 has been regenerated, the apparatus is returned to the normal state. In the foregoing processing apparatus, desorbed ammonia is not supplied to the second purifying chamber 30. Therefore, the non-ammonia purifying unit can reliably be protected from ammonia to prevent deterioration in function.

Figure 12:
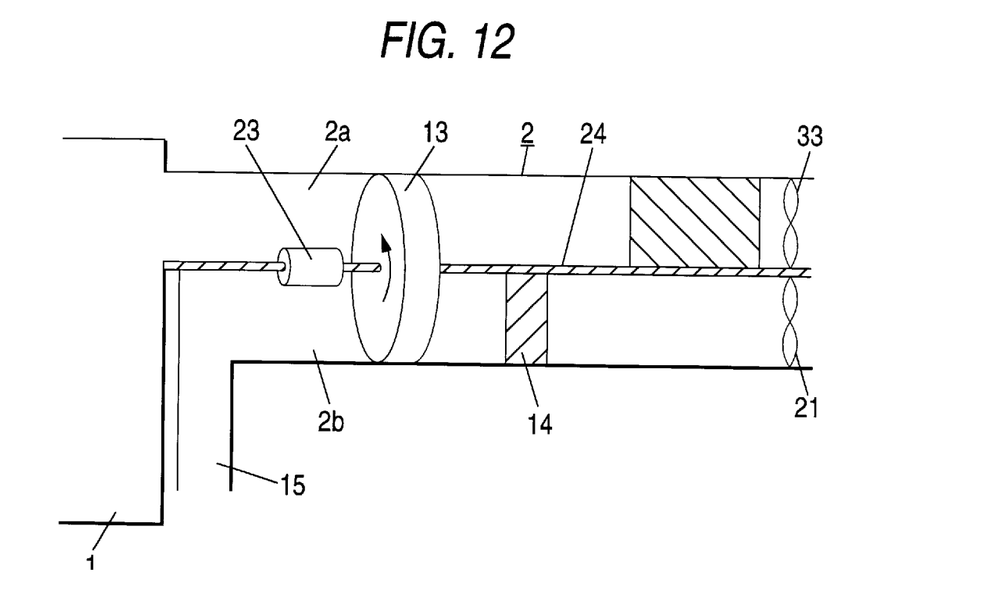
FIG. 12 is a schematic view showing an essential portion of the garbage disposal apparatus according to the embodiment of the present invention.

FIG. 12 is a schematic view showing an essential portion of a garbage disposal apparatus according to another embodiment of the present invention. As shown in FIG. 12, the processing apparatus has a structure such that the purifying chamber 2 is divided into a purifying passage 2*a* and a regeneration passage 2*b* by a partition plate 24 disposed along the direction in which gas flows. The adsorbent layer 13 is formed to transverse the purifying passage 2*a* and the regeneration passage 2*b*. The adsorbent layer 13 is provided with a drive unit 23. The purifying passage 2*a* is provided with a second purifying chamber 30 into which gas containing the malodorous components is introduced from the processing chamber 1 and which has the adsorbent layer 13 and the non-ammonia purifying unit. The regeneration passage 2*b* is isolated from the processing chamber 1 and provided with the inlet opening 15, the adsorbent layer 13 and the catalyst layer 14 for ammonia. The foregoing apparatus is characterized in that the drive unit 23 is operated so that the adsorbent layer 13 is rotated relative to a central shaft provided for the partition plate 24. Since the adsorbent layer 13 is rotated, adsorption is always performed by the adsorbent layer 13 moved to the purifying passage 2*a*. The portion of the adsorbent layer 13 moved to the regeneration passage 2*b* is regenerated. It is not required to operate the opening/closing means of the foregoing processing apparatus to perform opening and closing.

In the case where the adsorbent layer 13 includes a noble metal or a metal oxide for forming the catalyst layer 14 for ammonia, the adsorbent layer 13 may also serve as the catalyst layer 14 for ammonia. Usually, the foregoing processing apparatus is structured such that ammonia is adsorbed by the adsorbent of the adsorbent layer 13. When the adsorbent layer 13 is heated at the time of regenerating the same, desorbed ammonia is oxidized and decomposed by the noble metal or the metal oxide. Since the foregoing processing apparatus has the structure such that the adsorbent layer 13 also serves as the catalyst layer 14 for ammonia, the apparatus can be simplified.

Figure 13:
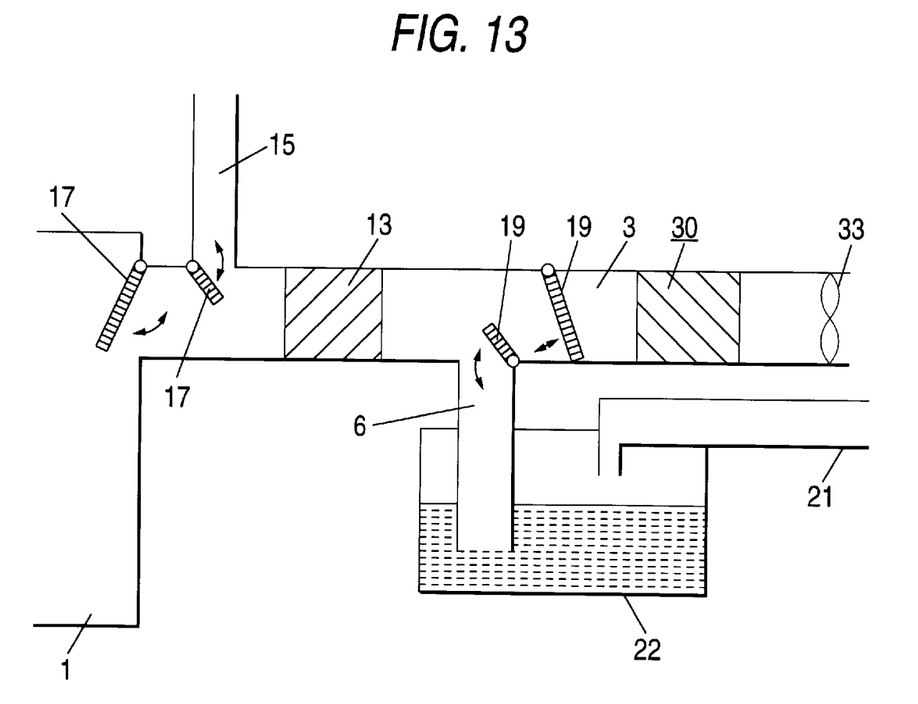
FIG. 13 is a schematic view showing an essential portion of the garbage disposal apparatus according to the embodiment of the present invention.

The first purifying chamber 10 for purifying ammonia is not limited to the foregoing embodiments. In an example case of the apparatus shown in FIG. 13 in which the gas-flow passage 3 connected to the second purifying chamber 30 and the gas-flow passage 6 for the regeneration are branched, a water tank 22 storing water solution is provided in place of the catalyst layer 14 for ammonia. When regeneration is performed, gas allowed to pass through the adsorbent layer 13 of the water tank 22 may be introduced so as to be dissolved in the water solution in order to regenerate the adsorbent layer 13.

Figure 14:
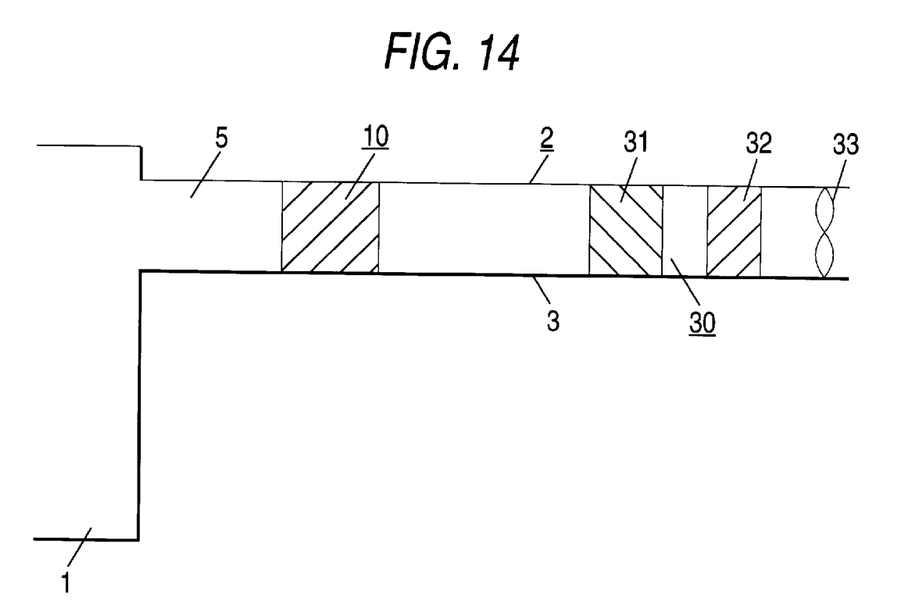
FIG. 14 is a schematic view showing an essential portion of the garbage disposal apparatus according to the embodiment of the present invention.

The second purifying chamber 30 for purifying non-ammonia gas will now be described. The non-ammonia purifying unit provided with the second purifying chamber 30 has a function of removing non-ammonia gas contained at a low concentration and having a small threshold after ammonia has been removed. The non-ammonia gas components are selected from a sulfur component such as methyl sulfide, methyl mercaptan and methyl disulfide; aldehyde; and alcohols. FIG. 14 is a schematic view showing an essential portion of a garbage disposal apparatus according to another embodiment of the present invention. The non-ammonia purifying unit is selected from an adsorbent layer 31 for non-ammonia having an adsorbent such as activated charcoal; and a catalyst layer 32 for non-ammonia composed of a catalyst having oxidizing performance. Each of the foregoing components may be used solely or use of their combination is permitted. Since the activated charcoal exhibits excellent efficiency for removing non-ammonia gas and it can easily be handled, it is a suitable material. Although the shape of the adsorbent layer 31 for non-ammonia may be in the form of a particle-type layer or a honeycomb shape, the honeycomb shape is a preferred shape because pressure damage can be prevented and excellent contact with the gas can be realized. The catalyst for forming the catalyst layer 32 for non-ammonia is selected from a structure in which the carrier includes at least any one of a noble metal, such as platinum, gold, silver, copper, palladium, ruthenium and rhodium or a metal oxide, such as nickel oxide, manganese oxide, cobalt oxide, iron oxide and vanadium pentoxide.

As described above, the garbage disposal apparatus according to the present invention has the structure such that the first purifying chamber 10 first removes ammonia contained in a large quantity; and then the second purifying chamber 30 removes the non-ammonia gas. Therefore, the non-ammonia purifying unit cannot be damaged by ammonia and the like. Therefore, the function of the non-ammonia purifying unit can satisfactorily be maintained for a long time.

Results of measurement of the purifying effect of the purifying unit will now be described. The measurement was performed as follows: garbage having a predetermined composition was decomposed with microorganisms in the processing chamber 1. Generated malodorous gas was purified in the purifying chamber 2. At this time, a sensory evaluation test was performed such that gas discharged from the outlet opening of the purifying chamber 2 was sniffed by six panellers. The sensory evaluation was performed by giving six step intensities of the smell such that the upper and lower values were omitted and an average of the four residual panellers were employed. The intensity of the smell was evaluated such that None was given zero point, Subtle was given one point, Slight smell with which the source can be determined was given two points, Fair smell which can easily be sensed was given three points, strong smell was given four points and Harsh smell was given five points. Note that the gas generated from the processing chamber 1 was a gas given five points.

EXAMPLE 1

The purifying chamber 2 having the structure shown in FIG. 2 was used to perform purification. The water storage tank 12 storing water 11a was employed as the first purifying chamber 10, and the activated charcoal was employed in the adsorbent layer 31 for non-ammonia in the second purifying chamber 30. The malodorous gas generated 60 to 80 minutes afterwards was smelled by the panellers. The average value of results was 1.5.

EXAMPLE 2

Purification was performed in the purifying chamber 2 having the structure shown in FIG. 9. Silica gel was used in the adsorbent layer 13 of the first purifying chamber 10. As the catalyst layer 14 for ammonia in the branched gas-flow passage 6, a structure in which platinum was included with alumina was employed. Activated charcoal was employed as the gas-flow passage 3 in the second purifying chamber 30. The malodorous gas was smelled by the panellers 60 to 80 minutes after the generation. The average value of results of the panellers was 1.0, and an average value of results of 1.1 was obtained three hours later.

EXAMPLE 3

In place of silica gel in Example 2, synthesized zeolite was used as the adsorbent layer 13 and a similar method to that according to Example 2 was employed to measure the effect. The malodorous gas was smelled by the panellers 60 to 80 minutes after the generation. The average value of results was 1.6, and an average value of results of 2.8 was obtained three hours later. Then, the opening/closing means 17 and 19 were operated, the adsorbent layer 13 and the catalyst layer 14 for ammonia were heated to 200° C., ammonia adsorbed to the adsorbent layer 13 was desorbed to regenerate the adsorbent layer 13. Then, the purification was restarted. The average value of results of the panellers was 1.7 which was a satisfactory value.

COMPARATIVE EXAMPLE 1

Purification was performed in a purifying chamber having only the activated charcoal which was a non-ammonia adsorbing layer. The average results of the panellers 60 to 80 minutes after the generation of the malodorous gas was 4.6.

COMPARATIVE EXAMPLE 2

Purification was performed in a purifying chamber having only the silica gel which was a non-ammonia adsorbing layer. The average results of the panellers 60 to 80 minutes after the generation of the malodorous gas was 5.0.

COMPARATIVE EXAMPLE 3

Purification was performed in a purifying chamber having only platinum heated the 200° C. The average results of the panellers 60 to 80 minutes after the generation of the malodorous gas was 2.0.

The garbage disposal apparatus of the present invention has the structure such that ammonia contained at a high concentration and having a large threshold is first removed in the first purifying chamber 10, and then non-ammonia gas contained at a low concentration and having a small threshold is removed in the second purifying chamber 30. Therefore, an excellent purifying efficiency can be realized. Moreover, the excellent performance can be maintained for a long time.

The garbage disposal apparatus of the present invention has the structure such that the dehumidifying unit 4 is provided in the gas-flow passage 3. Therefore, in addition to the foregoing effect, deterioration in the function of the non-ammonia purifying unit due to moisture can be prevented.

The garbage disposal apparatus of the present invention has the structure such that ammonia is desorbed from the adsorbent layer 13 and the adsorbent layer 13 can be regenerated, and required performance can be maintained for a long time in addition to the foregoing effects.

The garbage disposal apparatus of the present invention has the structure such that the gas-flow passage 6 having the catalyst layer 14 for ammonia and the gas-flow passage 3 connected to the second purifying chamber 30 are branched and the opening/closing means 19 for arbitrarily introducing/stopping gas is formed. In addition to the foregoing effects, the non-ammonia purifying unit can be protected and deterioration in the function can be prevented.

The garbage disposal apparatus of the present invention has the structure in which the adsorbent layer 13 is able to also serve as the catalyst layer 14 for ammonia. In addition to the foregoing effects, the apparatus can be simplified.

What is claimed is:

1. A garbage disposal apparatus comprising:

a processing chamber for processing garbage, the process of garbage in said processing chamber being performed by decomposition using microorganisms; and a purifying chamber for purifying gas discharged from the processing chamber, said gas containing malodorous ammonia and non-ammonia components, said purifying chamber including:

a first purifying chamber contiguously connected to said processing chamber and provided with an ammonia purifying unit for purifying ammonia; and a second purifying chamber, into which gas after passing through said first purifying chamber is introduced, including a non-ammonia purifying unit for purifying non-ammonia gas;

wherein said first purifying chamber has a water storage tank for one of storing water and water solution, and gas discharged from said processing chamber is introduced using an introduction device into said one of water and water solution of said water storage tank to purify ammonia; and a dehumidifying unit provided in a gas-flow passage connecting said first purifying chamber and said second purifying chamber to each other.

2. A garbage disposal apparatus according to claim 1, wherein said first purifying chamber includes said introduction device for bringing ammonia into contact with one of water and water solution.

3. A garbage disposal apparatus according to claim 2, wherein said water solution which is brought into contact with ammonia includes water solution containing cation exchange resin.

4. A garbage disposal apparatus according to claim 2, wherein said water solution which is brought into contact with ammonia includes acid water solution.

5. A garbage disposal apparatus according to claim 1, wherein said non-ammonia purifying unit has an adsorbent layer for non-ammonia.

6. A garbage disposal apparatus according to claim 5, wherein an adsorbent for forming said adsorbent layer for non-ammonia includes activated charcoal.

7. A garbage disposal apparatus according to claim 5, wherein said non-ammonia purifying unit has a catalyst layer for non-ammonia made of a catalyst having oxidizing performance.

8. A garbage disposal apparatus according to claim 7, wherein said catalyst is in a form in which a carrier includes at least one of a noble metal selected from the group consisting of platinum, gold, silver, copper, palladium, ruthenium and rhodium and a metal oxide selected from the group consisting of nickel oxide, manganese oxide, cobalt oxide, iron oxide and vanadium pentoxide.

9. The garbage disposal apparatus according to claim 2, wherein said unit comprises:

an introduction passage leading from said processing chamber to said water storage tank of said first purifying chamber; and wherein a leading end of said introduction passage reaches an inside portion of said at least one of water and water solution stored in said water storage tank, such that said gas discharged from said processing chamber is introduced directly into said at least one of water and water solution.

10. The garbage disposal apparatus according to claim 1, further comprising an ultrasonic device for applying ultrasonic vibrations to said at least one of water and water solution in said water storage tank of said first purifying chamber.

11. The garbage disposal apparatus according to claim 1, further comprising:

a fibrous layer, disposed in said at least one of water and water solution in said water storage tank of said first purifying chamber, said fibrous layer transversing said first purifying chamber, such that said gas discharged from said processing chamber passes through said fibrous layer.

12. A garbage disposal apparatus comprising:

a processing chamber for processing garbage, the process of garbage in said processing chamber being performed by decomposition using microorganisms; and a purifying chamber for purifying gas discharged from the processing chamber, said gas containing malodorous ammonia and non-ammonia components, said purifying chamber including:

a first purifying chamber connected to said processing chamber, and provided with an ammonia purifying unit for purifying ammonia; and a second purifying chamber, into which gas after passing through said first purifying chamber is introduced, including a non-ammonia purifying unit for purifying non-ammonia gas;

an ammonia adsorbent layer for adsorbing ammonia, said ammonia adsorbent layer being provided with said first purifying chamber;

a non-ammonia adsorbent layer for adsorbing non-ammonia, said non-ammonia adsorbent layer being provided with said second purifying chamber; and a catalyst layer for either one of ammonia and non-ammonia being provided downstream from at least one of said corresponding ammonia adsorbent layer and non-ammonia adsorbent layer.

13. A garbage disposal apparatus according to claim 12, further comprising:

an introduction passage for introducing gas discharged from said processing chamber into said ammonia adsorbent layer;

an inlet opening provided with said introduction passage for introducing outside air into said introduction passage; and first opening/closing means for arbitrarily introducing/stopping one of said outside air from said inlet opening and said gas introduced from said introduction passage.

14. A garbage disposal apparatus according to claim 13, wherein said purifying chamber is divided into a purifying passage and a regeneration passage by a partition plate, said ammonia adsorbent layer formed to traverse said purifying passage and said regeneration passage being rotated around a central shaft provided for said separation plate, said purifying passage being provided with said second purifying chamber having said ammonia adsorbent layer and a non-ammonia purifying unit, and said regeneration passage has said inlet opening, said ammonia adsorbent layer and said catalyst layer for ammonia.

15. A garbage disposal apparatus according to claims 12 or 13, wherein a plurality of purifying units each including said first purifying chamber and said second purifying chamber are disposed in parallel with respect to said processing chamber.

16. A garbage disposal apparatus according to any one of claims 1 and 12 further comprising:

a heating unit for heating said first purifying chamber.

17. A garbage disposal apparatus according to claim 12, wherein an ammonia adsorbent forming said adsorbent layer is selected from the group consisting of activated alumina, natural zeolite, synthetic zeolite, silica gel, activated clay, accretion activated charcoal and ion exchange resin.

18. A garbage disposal apparatus according to claim 12, wherein said catalyst layer for ammonia is formed in a carrier which includes a noble metal and a metal oxide.

19. A garbage disposal apparatus according to claim 18, wherein said noble metal is selected from the group consisting of platinum, gold, silver, copper, palladium, ruthenium and rhodium.

20. A garbage disposal apparatus according to claim 18, wherein said metal oxide is selected from the group consisting of nickel oxide, manganese oxide, cobalt oxide, iron oxide and vanadium pentoxide.

21. A garbage disposal apparatus according to claim 12, wherein said ammonia adsorbent layer includes one of a noble metal and metal oxide for forming said catalyst layer for ammonia, and said ammonia adsorbent layer also serves as said catalyst layer for ammonia.

22. A garbage disposal apparatus according to claim 12, wherein said non-ammonia purifying unit has an adsorbent layer for non-ammonia.

23. A garbage disposal apparatus according to claim 12, wherein an adsorbent for forming said adsorbent layer for non-ammonia includes activated charcoal.

24. A garbage disposal apparatus according to claim 12, wherein said non-ammonia purifying unit has a catalyst layer for non-ammonia made of a catalyst having oxidizing performance.

25. A garbage disposal apparatus comprising:
   a processing chamber for processing garbage, the process of garbage in said processing chamber being performed by decomposition using microorganisms; and
   a purifying chamber for purifying gas discharged from the processing chamber, said gas containing malodorous ammonia and non-ammonia components, said purifying chamber including:
      a first purifying chamber connected to said processing chamber, and provided with an ammonia purifying unit for purifying ammonia; and
      a second purifying chamber, into which gas after passing through said first purifying chamber is introduced, including a non-ammonia purifying unit for purifying non-ammonia gas;
   an adsorbent layer for adsorbing ammonia, said adsorbent layer being provided with said first purifying chamber;
   a catalyst layer for ammonia and non-ammonia provided downstream from said adsorbent layer in a gas-flow passage disposed between said first purifying chamber and said second purifying chamber;
   an introduction passage for introducing gas discharged from said processing chamber into said adsorbent layer;
   an inlet opening provided with said introduction passage for introducing outside air into said introduction passage; and
   first opening/closing means for arbitrarily introducing/stopping one of said outside air from said inlet opening and said gas introduced from said introduction passage.

26. A garbage disposal apparatus comprising:
   a processing chamber for processing garbage, the process of garbage in said processing chamber being performed by decomposition using microorganisms; and
   a purifying chamber for purifying gas discharged from the processing chamber, said gas containing malodorous ammonia and non-ammonia components, said purifying chamber including:
      a first purifying chamber connected to said processing chamber, and provided with an ammonia purifying unit for purifying ammonia; and
      a second purifying chamber, into which gas after passing through said first purifying chamber is introduced, including a non-ammonia purifying unit for purifying non-ammonia gas;
   an ammonia adsorbent layer for adsorbing ammonia, said ammonia adsorbent layer being provided with said first purifying chamber;
   a gas-flow passage provided between said first purifying chamber and said second purifying chamber, said gas-flow passage having an auxiliary gas-flow passage;
   a catalyst layer for ammonia arranged with said auxiliary gas-flow passage; and
   opening/closing means for arbitrarily introducing/stopping said gas after passing through said adsorbent layer to a gas-flow passage for introducing said gas after passing through said ammonia adsorbent layer to said second purifying chamber and said auxiliary gas-flow passage.

27. The garbage disposal apparatus according to claim 6, further comprising:
   a catalyst layer disposed in said auxiliary gas-flow passage.

28. A garbage disposal apparatus comprising:
   a processing chamber for processing garbage, the process of garbage in said processing chamber being performed by decomposition using microorganisms; and
   a purifying chamber for purifying gas discharged from the processing chamber, said gas containing malodorous ammonia and non-ammonia components, said purifying chamber including:
      a first purifying chamber connected to said processing chamber, and provided with an ammonia purifying unit for purifying ammonia; and
      a second purifying chamber, into which gas after passing through said first purifying chamber is introduced, including a non-ammonia purifying unit for purifying non-ammonia gas;
   an ammonia adsorbent layer for adsorbing ammonia, said ammonia adsorbent layer being provided with said first purifying chamber;
   wherein said non-ammonia purifying unit is a catalyst having oxidizing performance.

29. A garbage disposal apparatus comprising:
   a processing chamber for processing garbage, the process of garbage in said processing chamber being performed by decomposition using microorganisms; and
   a purifying chamber for purifying gas discharged from the processing chamber, said gas containing malodorous ammonia and non-ammonia components, said purifying chamber including:
      a first purifying chamber connected to said processing chamber, and provided with an ammonia purifying unit for purifying ammonia; and
      a second purifying chamber, into which gas after passing through said first purifying chamber is introduced, including a non-ammonia purifying unit for purifying non-ammonia gas;
   an ammonia adsorbent layer for adsorbing ammonia, said ammonia adsorbent layer being provided with said first purifying chamber; and
   a catalyst for either one of ammonia and non-ammonia being provided with said second purifying chamber.

* * * * *